(12) United States Patent
Selmi et al.

(10) Patent No.: US 9,351,926 B2
(45) Date of Patent: May 31, 2016

(54) IBUPROFEN INTRAVENOUS INFUSION

(71) Applicant: Pharmaceutical Solutions Industry Ltd., Jeddah (SA)

(72) Inventors: Khalil A. H. Selmi, Jeddah (SA); Irfan J. M. Jamil, Jeddah (SA); Yahya H. A. Idris, Jeddah (SA)

(73) Assignee: PHARMACEUTICAL SOLUTIONS INDUSTRY LTD., Jeddah (SA)

( * ) Notice: Subject to any disclaimer, the term of this patent is extended or adjusted under 35 U.S.C. 154(b) by 474 days.

(21) Appl. No.: 13/770,572

(22) Filed: Feb. 19, 2013

(65) Prior Publication Data

US 2013/0217772 A1 Aug. 22, 2013

(30) Foreign Application Priority Data

Feb. 20, 2012 (GC) ................................. 2012-20561

(51) Int. Cl.
  *A61K 9/00* (2006.01)
  *A61K 47/18* (2006.01)
  *A61K 31/192* (2006.01)
  *A61K 31/198* (2006.01)

(52) U.S. Cl.
  CPC ............. *A61K 9/0019* (2013.01); *A61K 31/192* (2013.01); *A61K 31/198* (2013.01); *A61K 47/183* (2013.01)

(58) Field of Classification Search
  CPC . A61K 9/0019; A61K 31/198; A61K 31/192; A61K 47/183
  USPC ......................................................... 514/565
  See application file for complete search history.

(56) References Cited

U.S. PATENT DOCUMENTS

2004/0132823 A1* 7/2004 Pavliv ............................ 514/565
2011/0028553 A1   2/2011 Pavliv et al.

OTHER PUBLICATIONS

HCWH, (Alternatives to Polyvinyl Chloride (PVC) and Di (2-Ethylhexyl) Phthalate Medical Devices on the European Market, http://noharm.org/lib/downloads/pvc/PVC_Alternatives_Europe.pdf, accessed Apr. 14, 2015, published 2006).*
Caldolor (Caldolor Ibuprofen Injection-Prescribing Information, http://www.caldolor.com/pdfs/Caldolor_Full_Prescribing_Information.pdf, accessed Apr. 14, 2015, published 2009).*
MPR (http://www.empr.com/caldolor-available-for-treatment-of-pain-and-fever/article/148424/, accessed Apr. 14, 2015, published Sep. 9, 2009).*
European Search Report, dated Jul. 23, 2013, from corresponding PCT application.
Morris et al., "A multi-center, randomized, double-blind, parallel, placebo-controlled trial to evaluate the efficacy, safety, and pharmacokinetics of intravenous ibuprofen for the treatment of fever in critically ill and non-critically adults", Critical Care, 2010, vol. 14, pp. 2-13, XP021085490.
Anonymous, "Caldolor Ibuprofen Injection-Prescribing Information", Caldolor, 2009, XP002705229.

* cited by examiner

*Primary Examiner* — Savitha Rao
*Assistant Examiner* — Angela Brown-Pettigrew
(74) *Attorney, Agent, or Firm* — Young & Thompson

(57) ABSTRACT

A novel pharmaceutical formulation includes a four mg per ml (4 mg/mL) Ibuprofen in an aqueous solution of Arginine and Ibuprofen, wherein the molar ratio of Arginine to ibuprofen is more than or equal to 1.000625:1, Tris buffered, isotonic, and adjusted to pH between 7.2-8.5 by addition of 1.0 N HCL, none of the excipients used contains material of animal or human origin. There were no novel excipients used. A method of treating through anti-inflammatory, analgesic, and antipyretic activity: fever, pain, dysmenorrhea and inflammatory diseases are also described. It is also used for pericarditis and patent ductus arteriosus (Patent ductus arteriosus (PDA)), relieve moderate to severe pain, dental pain and pain after an operation, mild to moderate pain including migraine headache, and for short term treatment of pyrexia in children over one year of age. The formulation is meant to be used as ready to use intravenous infusion.

11 Claims, 1 Drawing Sheet

R
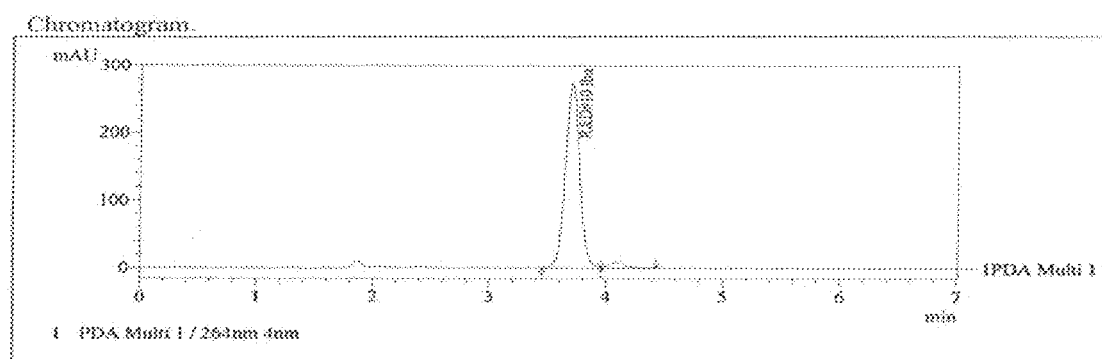
N
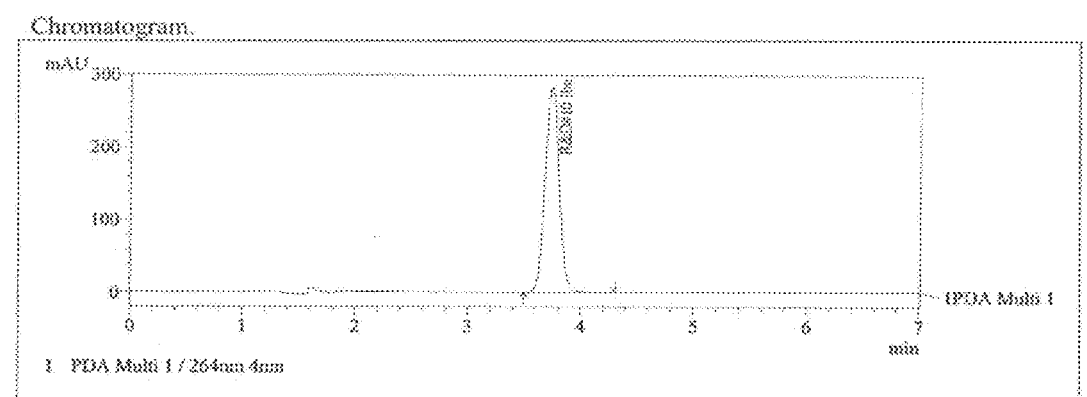

IBUPROFEN INTRAVENOUS INFUSION

DETAILED DESCRIPTION

Definition of the Relevant Field of the Invention

Human drugs (Pharmaceuticals), therapeutic class, Analgesics, Non-steroidal Anti-inflammatory Agents.

Professional Background of the Applicant

The product in question is a novel pharmaceutical formulation that compromises a 4 (milligram) mg/(milliliter) mL Ibuprofen in an aqueous solution and ready to use as an intravenous infusion.

At present, and in the markets, there is no available ready to use Ibuprofen 4 mg/mL intravenous infusion. The available one is Caldolor (100 mg/mL) injection, and it is not ready to use as well as declares that before using, it must be diluted.

Invention Introduction

Ibuprofen belongs to a group of drugs called non-steroidal anti-inflammatory drugs (also known as NSAIDs), which relieve pain and reduce inflammation (inhibitors of prostaglandin synthesis). Ibuprofen intravenous infusion, large volume injectable, contains 4 mg/mL of the active ingredient, Ibuprofen, in securely filled glass vial or non polyvinyl chloride bag. This medicine is a prescription-only (Rx Only). The commercially available Ibuprofen formulation Caldolor (100 mg/mL) injection, small volume injectable, is not read y to use, and declares that before using, it must be diluted and it should be used within 24 hours. The present new Ibuprofen (4 mg/mL) intravenous infusion solution is ready to use, whereas dilution is not required and the product is stable in terms of chemical, physical, and microbial (sterile and pyrogen free) for the whole shelf life. The product is a novel, stable and easy to use by medical professionals.

General specification of Ibuprofen 4 mg/mL: Clear, colorless to slightly yellow solution, filled in glass vial or in wrapped non polyvinyl chloride bag, sealed with rubber latex free, pH between 7.2 to 8.5, Arginine used as solubilizer, Tris as buffering agent, as well as isotonicity is guaranteed by Sodium Chloride usage, also none of the excipients used contains material of animal or human origin. There were no novel excipients used.

Finished product specification: Clear, colorless to slightly yellow solution without affecting its integrity, securely filled in clear glass vial with rubber stopper and flip off cap or in wrapped Non Polyvinyl Chloride "NPVC" bag, with Polypropylene Single Function Connector "SFC"-Port, Single Function Connector "SFC"-Cap & Polyisoprene Single Function Connector "SFC"-Rubber-Disc, pH between 7.2 to 8.5, Sterile, and Pyrogen free.

Technical Characteristics of the product available in Market—Caldolor (Ibuprofen) Injection (100 mg/mL), 400 mg/4 mL or 800 mg/8 mL, pharmaceutical dosage form, injectable filled in clear glass vials with rubber stopper and flip off cap (Small volume injectable). Caldolor consists of Ibuprofen, Arginine, and Water for Injection. Caldolor must be diluted up to volume (100 ml or 200 ml) prior to intravenous infusion, diluted solutions are stable up to 24 hours, at ambient temperature (approximately 25° C.) and room lighting, infusion time, for diluted injection, must be not less than 30 minutes. To be used under prescription (Rx Only), by qualified medical practitioner. Whilst Ibuprofen (Ibuprofen) Intravenous infusion (100 mg/mL), 200 mg/50 mL, 400 mg/100 mL, and 800 mg/200 mL, pharmaceutical dosage form, filled in clear glass vials with rubber stopper and flip off caps or in wrapped Non Polyvinyl Chloride "NPVC" bag, Polypropylene Single Function Connector "SFC"-Port, Single Function Connector "SFC"-Cap & Polyisoprene Single Function Connector "SFC"-Rubber-Disc (Large Volume Injectable).

Ibuprofen consists of Ibuprofen, Arginine, Tris, Sodium Chloride, and Water for Injection, ready to use. Stable at room temperature (approximately 30° C.) and room lighting for the whole shelf life (48 months), infusion time must be not less than 30 minutes. To be used under medical prescription (Rx Only), by qualified medical practitioner.

BRIEF DESCRIPTION OF THE DRAWINGS

FIG. 1 shows the chromatogram of Novel product (N) vs. reference Caldolor (R).

BEST APPROACHES TO CONDUCT THE INVENTION

Ibuprofen "(RS)-2-(4-(2-methylpropyl)phenyl) propanoic acid, CAS number: 15687-27-1" is the pharmaceutical grade active ingredient, and Arginine as solubilizer, Sodium Chloride as isotonic, Tris as buffer, Water for injection as vehicle, are the pharmaceutical grade inactive ingredients, none of the excipients used contains material of animal or human origin. There were no novel excipients used. Ibuprofen 4 mg/mL is ready to use, intravenous infusion, filled in clear Glass Vials or in wrapped Non Polyvinyl Chloride "NPVC" bag, Polypropylene Single Function Connector "SFC"-Port, Single Function Connector "SFC"-Cap & Polyisoprene Single Function Connector "SFC"-Rubber-Disc. in the Non Polyvinyl Chloride "NPVC", are used. Finished product proposed specification: Clear, colorless to slightly yellow solution, securely filled in clear glass vial with rubber stopper and flip off cap or in wrapped NPVC, Polypropylene SFC-Port, SFC-Cap & Polyisoprene SFC-Rubber-Disc. pH between 7.2 to 8.5. Sterile and Pyrogen free. Storage conditions: Store at room temperature, not more than 30° C. Store away from heat, moisture, and light. Keep product out of the reach of children.

Industrial Application of the Invention, Method of Manufacuring and Utilization

Composition of the preparation: Pharmaceutical grade Ibuprofen 400 mg, Arginine 340 mg, Tris 300 mg and Sodium Chloride 650 mg.

400 milligram (mg) of pharmaceutical grade Ibuprofen is dissolved in about 80 milliliter (ml) of water for injection and pharmaceutical grade: 340 milligram (mg) Arginine, 300 milligram (mg) of Tris buffer, and 650 milligram (mg) of Sodium Chloride and made up to 100 ml with water for injection. The pH was adjusted between 7.2 to 8.5 by addition of few drops of 1 N Hydrochloric Acid. The buffer is prepared by dissolving Tris in water for injection. Post filling, sterilize filled glass vials or non polyvinyl chloride bags at 121° C. for 20 minutes. The isotonicity was achieved by using the above composition. Filled vials and bags are transferred into Sterilizer under 121 C grade centigrade for 20 minutes. (see FIG. 1, as example for chemical test of Novel product (N) vs. reference Caldolor (R)). Application of above preparation in the form of intravenous infusion ready to use, without dilution.

Indications and Usage

This medicine to be dispensed under medical prescription only. Ibuprofen is used primarily for fever, pain, dysmenorrhea and inflammatory diseases such as rheumatoid arthritis It is also used for pericarditis and patent ductus arteriosus (Patent ductus arteriosus (PDA)). Ibuprofen 4 mg/mL intravenous infusion is indicated for the management of mild to moderate pain and management of moderate to severe pain as an adjunct to opioid analgesics, and for the reduction of fever in adults. Ibuprofen intravenous infusion is contraindicated in patients with known hypersensitivity to Ibuprofen or other NSAIDs, patients with asthma, urticaria, or allergic type reactions after taking aspirin or other NSAIDs. Ibuprofen Intravenous infusion is contraindicated for use during the perioperative period in the setting of coronary artery bypass graft (CABG) surgery. Ibuprofen Intravenous infusion should be used with caution in patients with prior history of ulcer disease or GI bleeding, in patients with fluid retention or heart failure, in the elderly, those with renal impairment, heart failure, liver impairment, and those taking diuretics or ACE inhibitors. Blood pressure should be monitored during treatment with Ibuprofen Intravenous infusion. Due to its broad indication, Ibuprofen Intravenous infusion is being used by physicians in a wide variety of settings to treat pain and fever in hospitalized patients. This includes a growing number of anesthesiologist who is using Ibuprofen intravenous infusion at induction of analgesia to preemptively address pain and inflammation associated with surgical procedures.

Ibuprofen 4 mg/mL intravenous infusion is used to treat conditions affecting the joints and muscles such as: swollen joints, frozen shoulder, low back pain, rheumatoid arthritis, (including juvenile rheumatoid arthritis or Still's disease ankylosing spondylitis (inflammation of the spine), osteoarthritis, other disorders of the muscles, bones and tendons, Ibuprofen 4 mg/mL intravenous infusion can also be used: in soft tissue injuries such as sprains and strains, to relieve mild to moderate pain in dysmenorrhoea (period pain), dental pain and pain after an operation, to relieve mild to moderate pain due to headache; including migraine headache, for short term treatment of pyrexia (fever) in children over one year of age.

Posology and method of administration: Undesirable effects may be minimized by using the lowest effective dose for the shortest duration necessary to control symptoms. Adults: the recommended dosage of Ibuprofen (4 mg/mL) intravenous infusion is 1200-1800 mg daily in three to four divided doses. Some patients can be maintained on 600-1200 mg daily. Children 8-12 years: Two (400-800 mg) three to four divided doses in 24 hours. For juvenile rheumatoid arthritis the usual daily dosage is 30-40 mg/kg/day in three to four divided doses.

Elderly: The elderly are at increased risk of the serious consequences of adverse reactions.

If Ibuprofen intravenous infusion is considered necessary, the lowest effective dose should be used and for the shortest possible duration. The patient should be monitored regularly for GI bleeding during NSAID therapy. If renal or hepatic function is impaired the dosage should be assessed individually.

Pharmacological Properties: Pharmacodynamic Properties

Ibuprofen is a propionic acid derivative with analgesic, anti-inflammatory and anti-pyretic activity. The drug's therapeutic effects as non-steroidal anti-inflammatory drugs (also known as NSAIDs) are thought to result from its inhibitory effect on the enzyme cyclo-oxygense, which results in a marked reduction in prostaglandin synthesis. Experimental data suggest that ibuprofen may inhibit the effect of low dose aspirin on platelet aggregation when they are dosed concomitantly. In one study, when a single dose of Ibuprofen 400 mg was taken within 8 hours before or within 30 minutes after immediate release aspirin dosing (81 mg), a decreased effect of aspirin on the formation of thromboxane or platelet aggregation occurred. However, the limitations of these data and the uncertainties regarding extrapolation of ex vivo data to the clinical situation imply that no firm conclusions can be made for regular ibuprofen use, and no clinically relevant effect is considered to be likely for occasional ibuprofen use.

Pharmacological Properties: Pharmacokinetic Properties-Mechanism of Action

Ibuprofen's mechanism of action, like that of other NSAIDs, is not completely understood but may be related to prostaglandin synthetase inhibition. Ibuprofen possesses anti-inflammatory, analgesic, and antipyretic activity.

Pharmacokinetics: Ibuprofen is a racemic mixture of [−]R- and [+]S-isomers. In vivo and in vitro studies indicate that the [+]S-isomer is responsible for clinical activity. The HR-form, while thought to be pharmacologically inactive, is slowly and incompletely (~60%) interconverted into the active [+]S species in adults. The [−]R-isomer serves as a circulating reservoir to maintain levels of active drug.

Ibuprofen, like most NSAIDs, is highly protein bound (>99% bound at 20 mcg/mL). Protein binding is saturable, and at concentrations >20 mcg/mL binding is nonlinear. Based on oral dosing data, there is an age- or fever-related change in volume of distribution for ibuprofen. Pharmacokinetic data; Bioavailability 49-73%, Protein binding 99%, Metabolism Hepatic (CYP2C9), Half-life 1.8-2 h, and Excretion Renal.

Ibuprofen is rapidly absorbed from the gastrointestinal tract. Peak serum concentrations occur 45 minutes after ingestion if taken on an empty stomach. When taken with food, peak levels are observed 1-2 hours after administration. The elimination half-life is approximately 2 hours. Ibuprofen is metabolised in the liver to two inactive metabolites and these, together with unchanged ibuprofen, are excreted by the kidney either as such or as conjugates. Excretion by the kidney is both rapid and complete. Ibuprofen is extensively bound to plasma proteins. In limited studies, Ibuprofen appears in the breast milk in very low concentrations Contraindications: Hypersensitivity to Ibuprofen or to any of the excipients in the product, Active or history of recurrent peptic ulcer/haemorrhage (two or more distinct episodes of proven ulceration or bleeding) or chronic dyspepsia, Ibuprofen Intravenous infusion is contraindicated in patients who have previously shown hypersensitivity reactions (e.g. asthma, rhinitis, angioedema or urticaria) in response to ibuprofen, aspirin or other non-steroidal anti-inflammatory drugs (NSAIDs), Severe heart failure, renal failure and hepatic failure, During the last trimester of pregnancy, History of gastrointestinal bleeding or perforation, related to previous NSAIDs therapy.

Special warnings and precautions for use: Undesirable effects may be minimized by using the lowest effective dose for the shortest duration necessary to control symptoms, and GI and cardiovascular risks below, The use of Ibuprofen intravenous infusion with concomitant NSAIDs including cyclooxygenase-2 selective inhibitors should be avoided, Elderly: The elderly have an increased frequency of adverse reactions to NSAIDs especially gastrointestinal bleeding and perforation which may be fatal. Respiratory disorders: Caution is required if administered to patients suffering from, or with a previous history of, bronchial asthma since NSAIDs have been reported to precipitate bronchospasm in such patients. Cardiovascular, Renal and Hepatic Impairment: The administration of an NSAID may cause a dose dependent reduction in prostaglandin formation and precipitate renal failure. Patients at greatest risk of this reaction are those with impaired renal function, cardiac impairment, liver dysfunction, those taking diuretics and the elderly. Renal function should be monitored in these patients. Cardiovascular and cerebrovascular effects: Appropriate monitoring and advice are required for patients with a history of hypertension and/or mild to moderate congestive heart failure as fluid retention and oedema have been reported in association with NSAID therapy. Clinical trial data suggest that use of ibuprofen, particularly at a high dose (2400 mg daily) and in long term treatment may be associated with a small increased risk of arterial thrombotic events (for example myocardial infarction or stroke). Overall, epidemiological studies do not suggest that low dose ibuprofen (e.g. 1200 mg daily) is associated with an increased risk of myocardial infarction, Patients with uncontrolled hypertension, congestive heart failure, established ischaemic heart disease, peripheral arterial disease, and/or cerebrovascular disease should only be treated with ibuprofen after careful consideration.

Similar consideration should be made before initiating longer-term treatment of patients with risk factors for cardiovascular events (e.g. hypertension, hyperlipidaemia, diabetes mellitus, and smoking.

SLE and mixed connective tissue disease: In patients with systemic lupus erythematosus (SLE) and mixed connective tissue disorders there may be an increased risk of aseptic meningitis.

Dermatological: Serious skin reactions, some of them fatal, including exfoliative dermatitis, Stevens-Johnson syndrome, and toxic epidermal necrolysis, have been reported very rarely in association with the use of NSAIDs. Patients appear to be at higher risk for these reactions early in the course of therapy; the onset of the reaction occurring in the majority of cases within the first month of treatment. Ibuprofen tablets should be discontinued at the first appearance of skin rash, mucosal lesions, or any other sign of hypersensitivity.

Impaired female fertility: There is limited evidence that drugs which inhibit cyclo-oxygenase/prostaglandin synthesis may cause impairment of female fertility by an effect on ovulation. This is reversible upon withdrawal of treatment. In women attempting to conceive or who are undergoing investigation of infertility, withdrawal of Ibuprofen should be considered.

Interaction With Other Medicinal Products and Other Forms of Interaction

Other analgesics including cyclooxygenase-2 selective inhibitors: Avoid concomitant use of two ormore NSAIDs (including aspirin) as this may increase the risk of adverse effects.

Care should be taken in patients treated with any of the following drugs as interactions have been reported in some patients. Antihypertensives: reduced antihypertensive effect, Diuretics: reduced diuretic effect. Diuretics can increase the risk of nephrotoxicity of NSAIDs, Cardiac glycosides: NSAIDs may exacerbate cardiac failure, reduce GFR and increase plasma cardiac glycoside levels, Lithium: Decreased elimination of lithium, Methotrexate: Decreased elimination of methotrexate, Ciclosporin: Increased risk of nephrotoxicity with NSAIDs, Mifepristone: NSAIDs should not be used for 8-12 days after mifepristone administration as NSAIDs can reduce the effects of mifepristone, Corticosteroids: Increased risk of gastrointestinal ulceration or bleeding, Anticoagulants: NSAIDs may enhance the effects of anti-coagulants, such as warfarin, Quinolone antibiotics: animal data indicate that NSAIDs can increase the risk of convulsions associated with quinolone antibiotics. Patients taking NSAIDs and quinolones may have an increased risk of developing convulsions, Anti-platelet agents and selective serotonin reuptake inhibitors (SSRIs): Increased risk of gastrointestinal bleeding.

Experimental data suggest that ibuprofen may inhibit the effect of low dose aspirin on platelet aggregation when they are dosed concomitantly. However, the limitations of these data and the uncertainties regarding extrapolation of ex-vivo data to the clinical situation imply that no firm conclusions can be made for regular ibuprofen use, and no clinically relevant effect is considered to be likely for occasional ibuprofen use, Tacrolimus: Possible increased risk of nephrotoxicity when NSAIDs are given with tacrolimus, Zidovudine: Increased risk of haematological toxicity when NSAIDs are given with zidovudine. There is evidence of an increased risk of haemarthroses and hematomas in HIV (+) haemophiliacs receiving concurrent treatment with zidovudine and ibuprofen, Pregnancy and Lactation: In view of the known effects of NSAIDs on the foetal cardiovascular system (risk of closure of ductus arteriosus), use in last trimester of pregnancy is contraindicated. The onset of labour may be delayed and the duration increased with an increased bleeding tendency in both mother and child. NSAIDs should not be used during the first two trimesters of pregnancy or labour unless the potential benefit to the patient outweighs the potential risk to the foetus. Lactation: In the limited studies so far available, NSAIDs can appears in the breast milk in very low concentrations, NSAIDs should, if possible, be avoided when breast-feeding. Effects on ability to drive and use machines, dizziness, drowsiness, visual disturbances, fatigue or headaches are possible undesirable effects after taking NSAIDs. If affected, patients should not drive or operate machinery.

Overdose In children ingestion of more than 400 mg/kg may cause symptoms. In adults the dose response effect is less clear cut. The half-life in overdose is 1.5-3 hours.

Symptoms Most patients who have ingested clinically important amounts of NSAIDs will develop no more than nausea, vomiting, epigastric pain, or rarely diarrhoea. Tinnitus, headache and gastrointestinal bleeding are also possible. In more serious poisoning, toxicity is seen in the central nervous system, manifesting as drowsiness, dizziness, excitation and disorientation, fainting or coma. Occasionally patients develop convulsions. In serious poisoning metabolic acidosis may occur and the prothrombin time/INR may be prolonged, probably due to interference with the actions of circulating clotting factors. Acute renal failure and liver damage may occur. Exacerbation of asthma is possible in asthmatics.

The invention claimed is:

1. A pharmaceutical composition, in a form ready-to-use for intravenous administration to a subject, comprising 4 mg/ml of Ibuprofen in an aqueous solution, tris-buffer and Arginine, the molar ratio of Arginine to Ibuprofen being in a range of from 1.000625:1 to 1.10:1, the composition being isotonic with body fluid of the subject and buffered at a physiological pH of 7.2 to 8.5.

2. The pharmaceutical composition according to claim 1, comprising 4 mg/ml of Ibuprofen, 3.4 mg/ml of Arginine, 3 mg/ml of Tris and 6.5 mg/ml of sodium chloride.

3. The pharmaceutical composition according to claim 1, wherein the composition is stable at room temperature and room lighting for 48 months.

4. The pharmaceutical composition according to claim 1, wherein the composition is packaged as Ibuprofen (mg)/aqueous solution (mL) selected from 100 mg/25 mL, 150 mg/37.5 mL, 200 mg/50 mL, 250 mg/62.5 mL, 300 mg/75 mL, 350 mg/87.5 mL, 400 mg/100 mL, 450 mg/112.5 mL, 500 mg/125 mL, 550 mg/137.5 mL, 600 mg/150 mL, 650 mg/162.5 mL, 700 mg/175 mL, 750 mg/187.5 mL, 800 mg/200 mL, 850 mg/212.5 mL, 900 mg/225 mL, 950 mg/237.5 mL, 1000 mg/250 mL, 1200 mg/300 mL, 1400 mg/350 mL, 1600 mg/400 mL, 1800 mg/450 mL, 2400 mg/600 mL, and 3200 mg/800 mL.

5. The pharmaceutical composition according to claim 1, further comprising sodium chloride.

6. The pharmaceutical composition according to claim 1, wherein the molar ratio of Arginine to Ibuprofen is in a range selected from 1.00125:1 to 1.10:1, 1.0025:1 to 1.10:1, 1.005:1 to 1.10:1, 1.01:1 to 1.10:1, 1.02:1 to 1.10:1, 1.03:1 to 1.10:1, 1.04:1 to 1.10:1, 1.05:1 to 1.10:1, 1.06:1 to 1.10:1, 1.07:1 to 1.10:1, 1.08:1 to 1.10:1, and 1.09:1 to 1.10:1.

7. The pharmaceutical composition according to claim 1, wherein the composition is packaged in a clear glass vial type I with a rubber stopper and a flip off cap.

8. The pharmaceutical composition according to claim 1, wherein the composition is packaged in a non-polyvinyl chloride bag, with a polypropylene single function connector port, a single function connector cap and a polyisoprene single function connector rubber-disc.

9. The pharmaceutical composition according to claim 1, further comprising hydrochloric acid.

10. The pharmaceutical composition according to claim 1, wherein the composition is stable at room temperature and room lighting for at least 48 months.

11. A method of treating through anti-inflammatory, analgesic, and antipyretic activity a condition selected from the group consisting of: rheumatoid arthritis, juvenile rheumatoid arthritis, Still's disease, ankylosing spondylitis, osteoarthritis and other non-rheumatoid (seronegative) arthropathies, non-articular rheumatic conditions, frozen shoulder (capsulitis), bursitis, tendinitis, tenosynovitis, swollen joints, low back pain and other disorders of the muscles, bones and tendons, soft tissue injuries, sprains and strains, relief of mild to moderate pain, dysmenorrhoea, dental and post-operative pain, headache, migraine headache, pain and fever in hospitalized patients, pyrexia in children over one year of age, pericarditis and patent ductus arteriosus (PDA), the method comprising administering to a subject in need thereof the pharmaceutical composition according to claim 1.

* * * * *